US007751999B1

(12) United States Patent
McAtee et al.

(10) Patent No.: US 7,751,999 B1
(45) Date of Patent: Jul. 6, 2010

(54) METHOD AND SYSTEM FOR FIELD CALIBRATING AN ION MOBILITY SPECTROMETER OR OTHER TRACE VAPOR DETECTION INSTRUMENT

(75) Inventors: Robert F. McAtee, Bloomington, IN (US); Michael A. Eagan, Washington, IN (US); Eric Wallis, Bloomington, IN (US); Norman Popkie, Jr., Rock Hill, SC (US); Matthew Todd Griffin, Fort Mill, SC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 26 days.

(21) Appl. No.: 12/076,540

(22) Filed: Mar. 19, 2008

Related U.S. Application Data

(63) Continuation of application No. 11/108,150, filed on Apr. 12, 2005, now abandoned.

(51) Int. Cl.
*G01N 27/00* (2006.01)
*G06F 17/40* (2006.01)
(52) U.S. Cl. .............................. 702/85; 702/23; 702/24; 702/30; 422/83; 422/119; 204/424
(58) Field of Classification Search .............. 702/22–24, 702/27, 30, 85
See application file for complete search history.

(56) References Cited

U.S. PATENT DOCUMENTS

| 4,257,439 | A | * | 3/1981 | Mayeaux ...................... 137/88 |
| 5,109,691 | A | * | 5/1992 | Corrigan et al. ............ 73/23.36 |
| 5,465,607 | A | * | 11/1995 | Corrigan et al. ............ 73/23.36 |
| 6,658,915 | B2 | * | 12/2003 | Sunshine et al. ............. 73/23.2 |
| 6,997,347 | B2 | * | 2/2006 | Peng et al. ..................... 222/3 |
| 7,078,680 | B1 | * | 7/2006 | Griffin et al. ................ 250/287 |
| 7,096,125 | B2 | * | 8/2006 | Padmanabhan et al. ....... 702/24 |
| 2004/0178917 | A1 | * | 9/2004 | Duan ......................... 340/632 |
| 2004/0216508 | A1 | * | 11/2004 | Hirsch et al. ................. 73/1.04 |
| 2005/0051719 | A1 | * | 3/2005 | Miller et al. ................ 250/287 |

* cited by examiner

*Primary Examiner*—Hal D Wachsman
(74) *Attorney, Agent, or Firm*—John Gladstone Mills; Mark O. Glut; U.S. Navy-NAVAIR-Nava Air Systems Command

(57) ABSTRACT

The present invention can be generally described as a vapor detection instrument testing system and testing process. This testing system integrates a computing system loaded with testing software, and a test-substance generating device. The present device is portable and provides a user with the ability to perform vapor detection instrument testing at the field side of the vapor detection instrument. The portability of the vapor detection instrument testing system results in more frequent instrument testing and less detection instrument down time.

1 Claim, 6 Drawing Sheets

METHOD AND SYSTEM FOR FIELD CALIBRATING AN ION MOBILITY SPECTROMETER OR OTHER TRACE VAPOR DETECTION INSTRUMENT

CROSS REFERENCE TO RELATED APPLICATIONS

This application is continuation of U.S. patent application Ser. No. 11/108,150 filed. Apr. 12, 2005 which is now abandoned.

STATEMENT REGARDING FEDERALLY SPONSORED RESEARCH OR DEVELOPMENT

The invention described herein may be manufactured and used by or for the Government of the United States of America for governmental purposes without payment of any royalties thereon or therefor.

REFERENCE TO A SEQUENCE LISTING, A TABLE, OR A COMPUTER PROGRAM LISTING COMPACT DISK APPENDIX

Not Applicable.

BACKGROUND OF THE INVENTION

Because of the growing need to protect people, property, and public transportation facilities, there has been increasing demand for detectors and other instruments designed to determine the presence of various substances including, but not limited to; chemicals typically used in explosives; hazardous or toxic materials; and other substances of interest, e.g. narcotics. Various methods, techniques and technologies are being utilized to ascertain the presence of these substances (or other materials of interest) including those based on vapor detection. Vapor detection technology capable of detecting very small (i.e. trace) amounts of substances, and a number of detectors (and other instruments) have been designed to use vapor detection, e.g. an Ion Mobility Spectrometer (IMS) is a type of detector that utilizes this technology. In general IMS is a simple, gas-phase ion separation technique in which ions are formed, manipulated, collected, and measured. Because of IMS's good sensitivity, low power requirements, and its ability to operate at atmospheric conditions, IMS has gained wide acceptance—especially in its use in field-portable trace chemical detectors.

Since this technology is widely used, and since the instruments (or other devices) utilizing this technology play an increasingly significant role in law enforcement, anti-terrorist, and force protection endeavors, it is vitally important that this detection equipment (or systems) be available for use, and that the user has a high level of confidence in the equipment's (or system's) performance. Generally, such confidence is achieved by calibrating the ion mobility spectrometer or other similar detection instrument in order to maintain the instrument in a tuned condition. However, many of these instruments require the use of National Institute of Standards and Technology (NIST) traceable methods (e.g., the use of NIST approved standards may be required to validate the calibration or, possibly, the reliability of the detection instrument). Furthermore, while the tasks of calibrating, testing, and/or maintaining a detection instrument in a controlled environment (such as a lab) is difficult enough, it is even more so in an out-of-doors environment. Even more troubling, is the issue that the technologies needed to field calibrate IMS detection instruments, or other technologies such as SAW or Mass Spectrometry, are not readily available to the community. Consequently, the performance of detection instrument testing and/or calibration are generally accomplished by removing the field units from service and returning them to a lab for testing and/or calibration, which may take the equipment out-of-service for an extended period, and which can be prohibitively expensive. Therefore, a need exists to provide a fast, accurate, and cost-effective method and/or system, which is capable of at least monitoring detection instrument (or other detection system) responses, and which can preferably perform any of its functions in the field.

BRIEF SUMMARY OF THE INVENTION

According to its major aspects and briefly recited, the present invention relates generally, but without limitation, to a system and method for providing a user with the ability to perform field-testing on a vapor detection instrument. This is generally accomplished by measuring an instrument's response to a known concentration of analyte, and the results thus obtained from the field-testing can then be used to "field calibrate" or "field test" the system. More specifically, the user may have the ability to perform a test device calibration of the detection instrument (or system), or at least be able to obtain a "confidence" check of the instrument's (system's) performance.

The inventive approach is based on providing at least one "standard" (i.e., known) concentration to the IMS, or other vapor detection instrument or system, determining the "actual response" to each such "standard," and then comparing the instrument's (or system's) "actual response" to a "known response" for each such "standard."

A feature of this invention is its portability, which provides the advantage of allowing performance checks in the field, i.e., the location where the instrument or system is located.

Other potential advantages of this portability include, but are not limited to: cost savings associated with not having to send an instrument/system to a lab to have its functionality checked (while still maintaining a high level of confidence in the instrument's/system's performance); decreased disruptions to homeland security and/or force protection (which should increase the user's defensive stance against hostile entities); and allowing for the capability to increase the frequency of checks of the dynamic range and response of an instrument/system, e.g., on even a daily basis.

Still another feature of this invention is its testing flexibility, which provides the advantage of being able to ensure optimal instrument/system performance and reliability over a wide range of analyte concentrations.

It is a further feature of the present invention to be functionally and operationally simple to use, yet be highly durable and reliable.

Other features and advantages will be apparent to those skilled in the art from a careful reading of the Detailed Description of the Invention, accompanied by the drawings.

DETAILED DESCRIPTION OF THE INVENTION

While the following discussion illustrates preferred embodiments of the present invention, it does not limit the present invention from being implemented (and/or configured) in a myriad of other manners within the spirit and scope of this Application. Moreover, while a portion of the devices, software, circuits, and/or other components used in the present invention preferably come from the group of devices, software, circuits, and/or other components that are well-known, and/or are commonly (or readily made) available, other means of implementing the present invention may also be used as well.

As background, a preferable embodiment of the present invention integrates software control of vapor generation with data collection and analysis. According to this preferred embodiment, the present invention would generate a response from a vapor (or other) detection instrument through the controlled introduction of a low concentration and a high concentration of an analyte (or other simulant), and would then analyze these responses to form a performance check of the instrument, which could be accomplished by performing at least a two-point check of the dynamic (i.e., useful) range (or by similarly testing for some other performance characteristic) of the instrument being tested. In other words, and simply stated, the present invention is capable of providing response graphs (or curves) to given concentrations of analyte (or other simulant) introduced to a vapor (or other) detection instrument. [Preferably, these graphs (or curves) are derived from the spectral signatures for a given calibrating material used with a specific instrument, and could cover a wide range of NIST traceable concentrations for which the instrument will be operated; however, other methods for the production of the graphs, curves or other responses can be used as well.]

The information provided by the present invention can then be utilized by the end-user, e.g., facility security or "first responder" personnel, in order to provide such user with a performance check of their vapor (or other) detection instrument. As examples, the present invention could possibly be used for the following: checking detection instrument (or system) sensitivity degradation; general detection instrument testing; detection instrument diagnostic testing; and/or instrument (or system) maintenance optimization.

Figure 1:
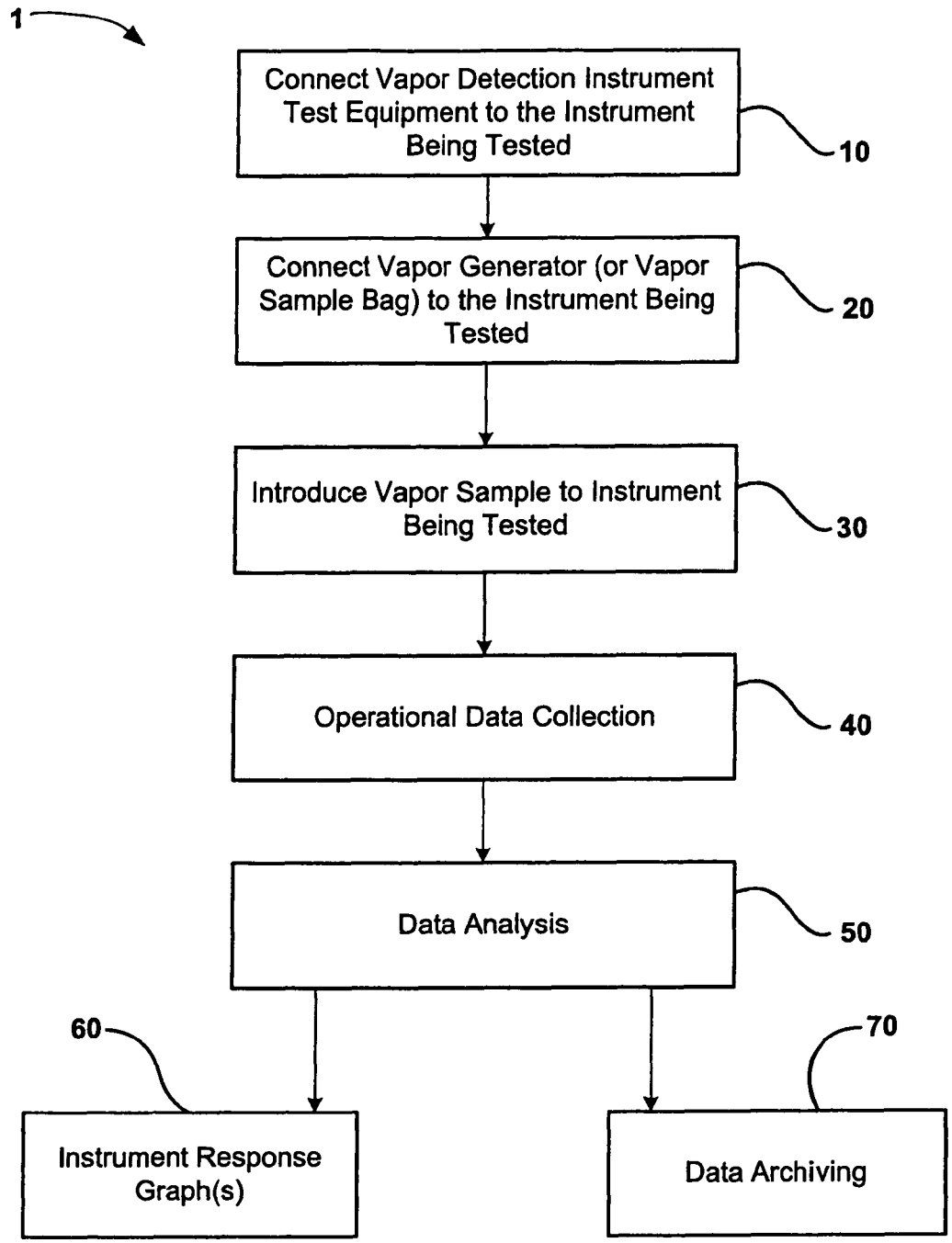
FIG. 1 is a block diagram illustrating a generic configuration of the process according to the preferred embodiment of the invention.
Figure 2:
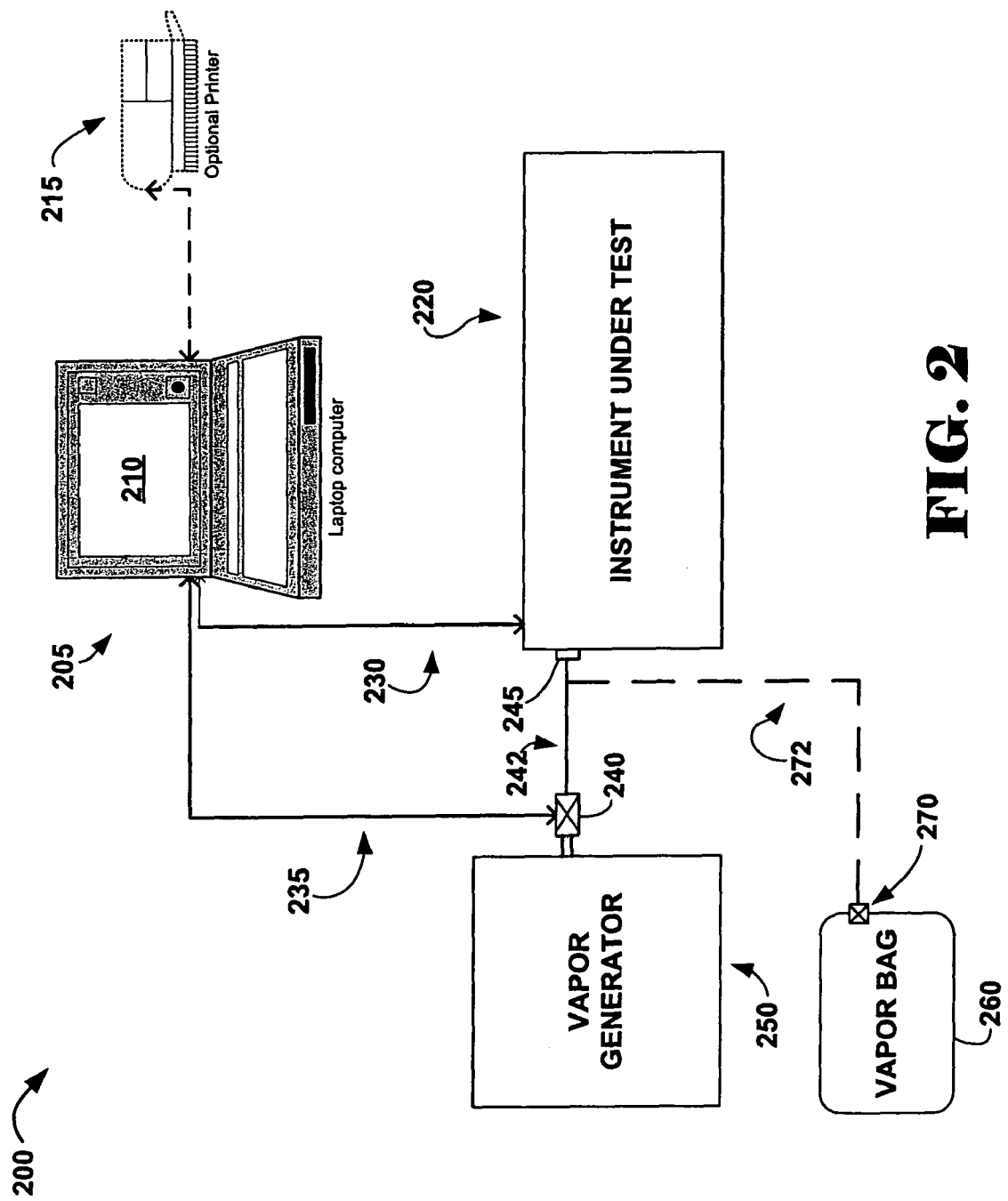
FIG. 2 is a block diagram illustrating a generic configuration of the system according to the preferred embodiment of the invention.

Referring now to FIG. 1 and FIG. 2, a block diagram illustrating a mode of operation of the present invention vapor detection instrument response test process (Process) 1, and an example of the vapor detection instrument test system (System) 200 itself, are shown. As shown, the Process 1 requires connecting the Test Equipment (i.e., the System 200) to the instrument, detector, or system to be tested as referred to by the "Connect Vapor Detection Instrument Test Equipment to the Instrument Being Tested" block 10. [Hereinafter, unless otherwise qualified, the terms instrument, detector, or system (either singly or collectively) will be referred to as instrument.] More specifically, and preferably, the System 200 is comprised of a laptop 205 (as shown in FIG. 2) or notebook computer system; however, other types of computing tools could be used as well including, but not limited to, commonly available computer workstations and/or other computers or computer systems.

Referring again to FIGS. 1 and 2, it is preferable, regardless of the computer system used that the computer system is constructed to be rugged or of an enhanced durability in order to facilitate its use in the field. Moreover, loaded onto the laptop 205 (or whatever computing system is used) would be software specifically written for the particular Instrument Under Test 220. This software could be used to control the testing or at least the collection 40 and analysis 50 of the data necessary to make the desired performance (or other appropriate) Instrument checks, and would preferably include instruction to perform diagnostic checks as well. Furthermore, the software may be written in any language, but it is preferably written in LabVIEW, C, C++, and/or JAVA, and the software may provide (or assist in providing) GUI screens, the graphs and/or other user displays necessary to operate the System 200 and/or its tests, as described below.

Referring still to both FIGS. 1 and 2, the interface or communications connection referred to (or required by) the "Connect Vapor Detection Instrument Test Equipment to the Instrument Being Tested" block 10, are preferably provided by using data acquisition electronics, which may utilize either a direct link (e.g., RS 232, TCP/IP, or any other appropriate item), or as an example could utilize wireless communications (e.g., Bluetooth, 802.11a/b/g, or any other appropriate technology). Preferably, afterwards, the source of a vapor sample (i.e., the "Standard Sample" or a test substance) is a vapor generator 250, which can be connected to the Instrument Under Test 220 and, if desired and if such connection is available, to the laptop 205 through a flow control valve 240. Preferably, the flow control valve 240 is a solenoid or other electro-mechanical valve; however, any other appropriate flow-control device could be used as well including, but not limited to, standard mechanical flow control valves (not shown), which clearly would not require a link to the laptop 205. In general, a vapor generator 250 is a machine capable of providing an appropriate "Standard Sample" (or test substance) to the Instrument Under Test 220. As an example, and preferably, a permeation-tube based vapor generator as described on the Kin-Tek website at: www.kin-tek.com could be used. And while a permeation-tube based vapor generator may be used, vapor generators are not limited to only this type, and, as an example, compressed gas cylinders, direct volatilization, or other similar techniques could be used as well. Importantly, however, is the applicants' belief that the application of permeation-tube type vapor generators to field portable uses is new to the field.

The connection of the vapor generator to the Instrument is represented by the "Connect Vapor Generator (or Vapor Sample Bag) to the Instrument Being Tested" block 20, and, as shown in FIG. 2, includes the use of a gas (or fluid) Connection Line 242 between the Vapor Generator 250 and the Instrument Under Test 220. Preferably, the Connection Line 242 connects the Vapor Generator 250 to the line fitting 245 on the Instrument Under Test 220 through the flow control valve 240. Moreover, it is also preferable that any surface in contact with the analyte being used for the "Standard Sample" (or test substance), e.g., any gas or fluid transfer line, such as the Connection Line 242 shown in FIG. 2, must be compatible with the analyte being generated and used. As a non-limiting example, for use of the invention to test IMS type Instruments the Connection Line 242 can be treated with Silcosteel® (and heated), which is available from the Restek Corporation (having a business address of: 110 Benner Circle Bellefonte, PA 16823-8812), and the o-rings in the flow control valve 240 can be made of Kalrez®, which is available from the E. I. Du Pont de Nemours and Company (having a business address of: 1007 Market St., Wilmington, DE 19898). Notably, however, and as previously mentioned, other analytes may be used, which may require the use of other materials for compatibility.

The next step in the Process 1 is the Introduce Vapor Sample to Instrument Being Tested 30. Preferably, the generation and/or the introduction of the "Standard Sample" (or test substance) is controlled (e.g., volume, concentration, and/or rate), and such control is preferably provided by the laptop 205 and its link to the flow control valve 240; however, other suitable means for the introducing (or injecting) the "Standard Sample" (or test substance) into the Instrument 30 can be used as well. For example, as an option, or as an alternative embodiment of the System 200, a Vapor Bag 260 containing a known volume and concentration of analyte can be used to generate (and/or introduce) the "Standard Sample" (or test substance) for checking the Instrument Under Test 220. Preferably, the Vapor Bag 260 is constructed of an analyte compatible material, is easy to transport and store, should be leak-proof, and it should have at least one gas or fluid transfer line connection fitting or connection valve 270 (to connect the Vapor Bag 260 through an optional connection line 272 to the line fitting 245 on the Instrument Under Test 220). Furthermore, the Vapor Bag 260 is preferably filled using an analyte (or other appropriate) generating device.

Figure 3:
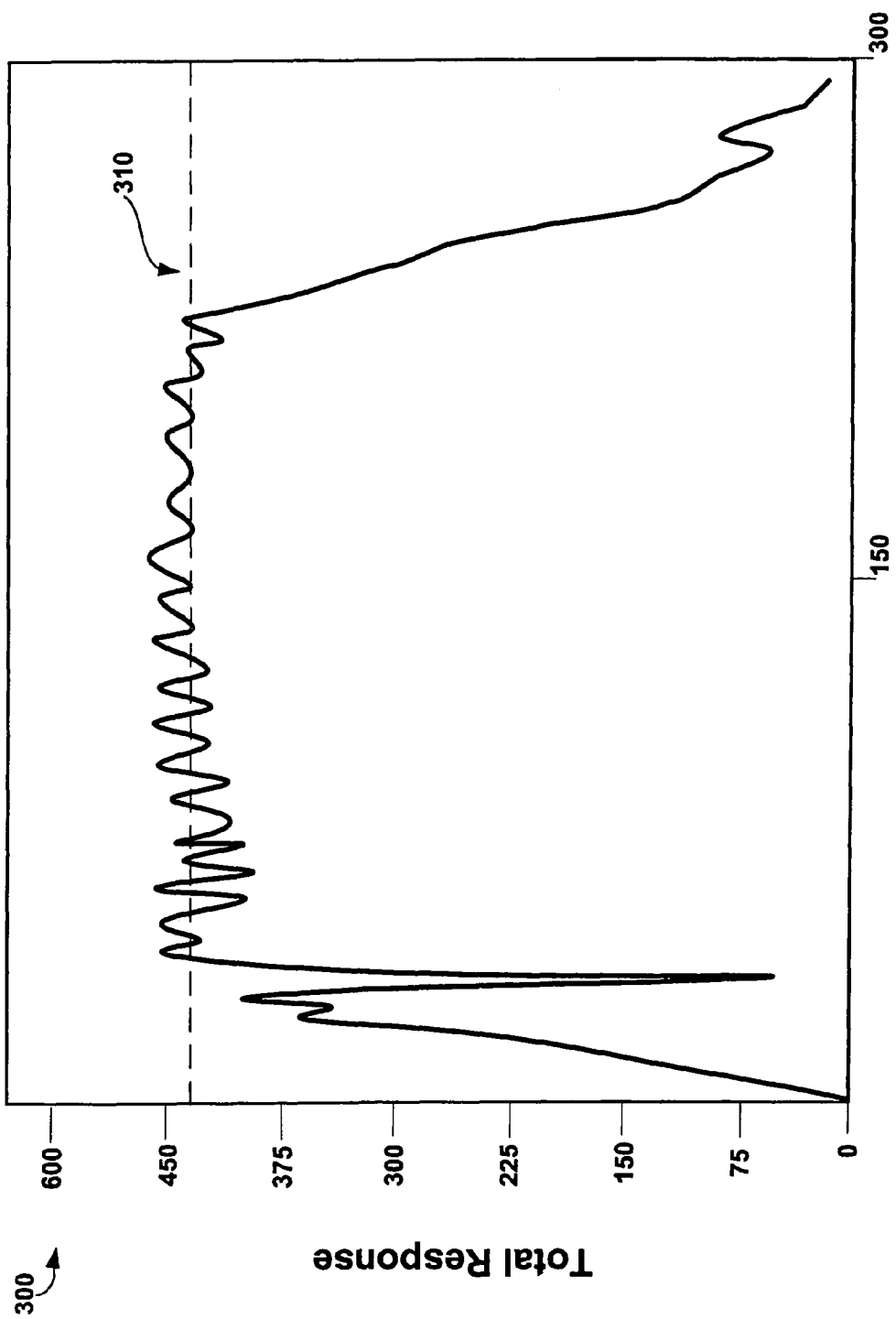
FIG. 3 is a graphical example of a typical detection instrument response to a simulant sample (as generated by the Process and System) according to a preferred embodiment of the present invention.

Once the "Standard Sample" (or test substance) is introduced to the Instrument Being Tested 30, the Instrument Under Test 220 is operated in its normal manner, and the data generated by the Instrument Under Test 220 is provided to the laptop 205 (as represented by the "Operational Data Collection" 40 block in FIG. 1). Using the hardware of, and the software loaded onto, the laptop 205, the laptop 205 performs "Data Analysis" 50, provides the user with one or more Instrument Response Graph(s) 60 (which may be shown on the monitor portion 210 of the laptop 205 and/or provided as a hard-copy by using an optional printer 215), and/or performs Data Archiving 70. More specifically with respect to the Data Analysis 50, this function is accomplished by using "data modules," which are portions of the software specifically written to receive, manipulate, and/or analyze the data from the Instrument Under Test 220. Moreover, these "data modules" are Instrument Under Test 220 technique dependent, and are written or built into the software driver for the particular Instrument Under Test 220 and loaded onto the laptop 205. As an example, if the Instrument Under Test 220 is a particular IMS-based device, the user would make the appropriate selection on the laptop's graphical user interface (not shown), and the laptop 205 would run the appropriate "data module" for that Instrument Under Test 220. In general, the "data modules" used for an IMS device, as an example, would preferably monitor (or sample) at least the monomer and dimer product peaks generated by the Instrument Under Test 220 and, in turn, may at least generate an output corresponding to a "total response" for the Instrument Under Test 220, or a "total instrument response" comprised of the monomer result plus two times the dimer response. This "total response" or "total instrument response" may then be provided to the user 60 as previously discussed. [An example of a Total Response graph 300 for an IMS's "sampled" response to dipropylene glycol methyl ether is shown in FIG. 3.] Moreover, regarding Data Archiving 70, the data is preferably stored on a database file associated with the subject test, and may be stored on the laptop 205 for future use; however, any other well known data archiving method could be used as well.

Figure 4:
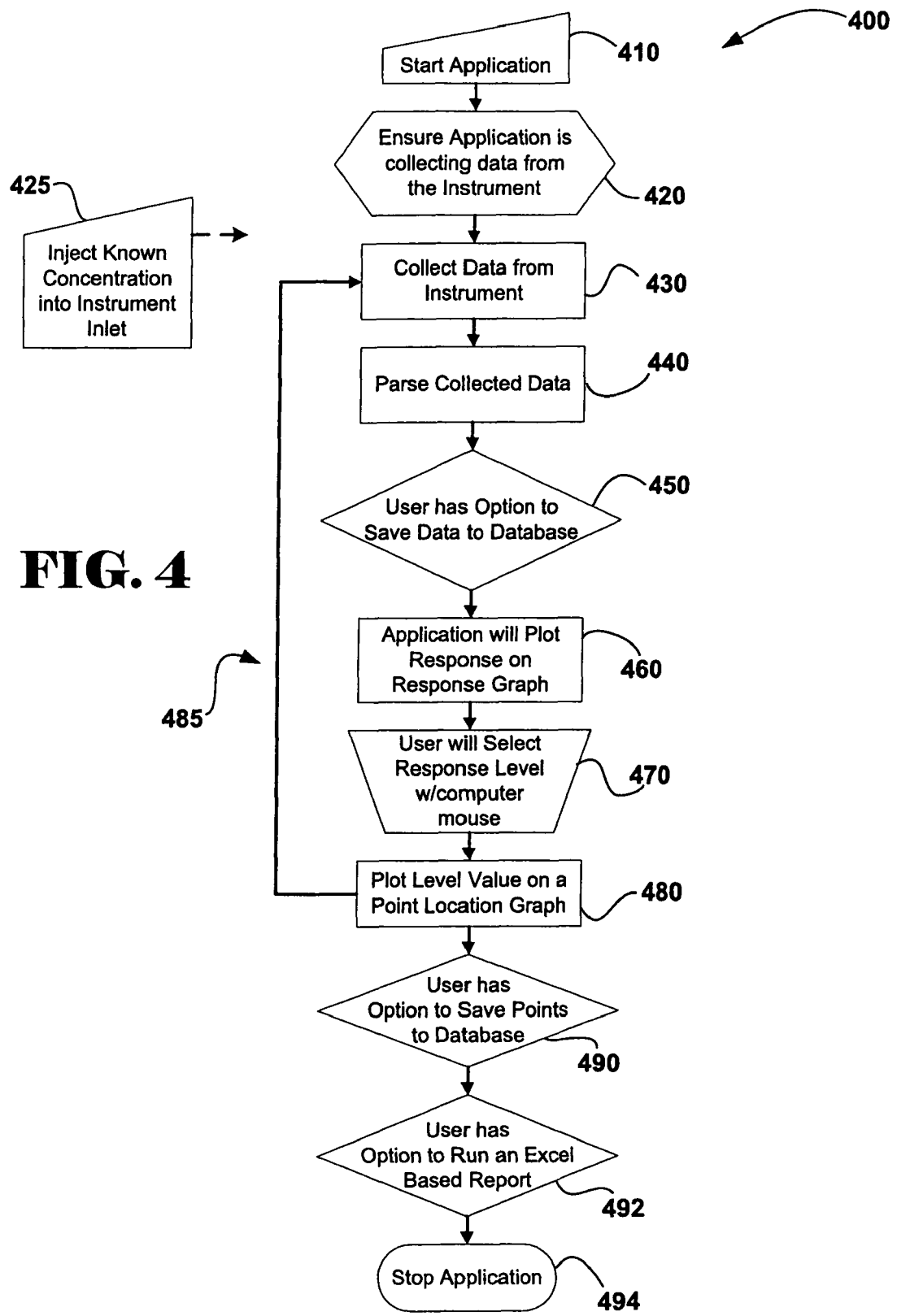
FIG. 4 is a flow chart illustrating a generic functional sequence of the System software according to a preferred embodiment of the present invention.

Referring now to FIGS. 1-6, a non-limiting example of the operation of the Process 1 and the System 200 from the perspective of the software is shown. More specifically, a "Two-Point Calibration" test 400 (TEST) is shown in FIG. 4; however, the flexibility of the Process 1 and the System 200 is not limited to using (two points or) only two points, i.e., a high concentration and a low concentration point, to check the Instrument Under Test 220 (INSTRUMENT). Furthermore, this example is based on performing the TEST 400, on a dual-cell INSTRUMENT 220, e.g., having both a G-type and a H-type cell; therefore, the TEST 400 will be performed using two simulants (i.e., a different stimulant to check each type of cell), and by using a low concentration and a high concentration of each simulant to produce a low response and a high response from each cell, as appropriate. However, since the Process 1 and the System 200 are flexible (i.e., they are characterized by a capability to adapt to new, different, or changing requirements), the Process 1 and/or the System 200 are capable of being used with (or for) detection instruments and systems having any number of cells or channels, i.e., the Process 1 and/or the System 200 are not limited to only being capable of testing single-cell or dual-cell detection instruments or systems.

The TEST 400, can be described by the following non-limiting description. First, the testing software (APPLICATION) that is loaded on the laptop 205 is started 410; next, as represented by the "Ensure Application is collecting data from the Instrument" block 420, the user verifies that the APPLICATION is collecting data from the INSTRUMENT 220 through the communications connections previously discussed—this is preferably a baseline response (or signal) associated with the INSTRUMENT 220 being properly configured and "on," but prior to introducing the "Standard Sample" (or test substance) to the INSTRUMENT 220. Afterwards, a known (preferably a low) concentration of stimulant (i.e., a "Standard Sample" or test substance) is introduced into the inlet of the INSTRUMENT 220 and responsive data is collected from the INSTRUMENT 220, as represented by the "Inject Known Concentration into Instrument Inlet" block 425, and the "Collect Data from Instrument" block 430. [ASIDE: In general, each manufacturer's detection instrument produces information (e.g., status mode of operation, results, and/or etc.) that can be transmitted to another device (such as a computer) using connections like RS232, and since these instruments generally transmit such information as blocks of data, such information/data would need to be parsed to determine actual message content.] Regarding this and continuing with the description, the collected data is then interpreted and/or manipulated by the software (preferably, by using coding in the APPLICATION specifically written to interact with the protocol used by the INSTRUMENT 220), as represented by the "Parse Collected Data" block 440. The user can then save the data collected, which is represented by the "User has Option to save Data to Database" block 450 and, if saved, the APPLICATION can use the data collected to provide the user with a Response Graph 300, as shown in FIG. 3, and as represented by the Application will Plot Response Graph" block 460. Then, while preferably viewing the Response Graph 300 on the monitor 210 (or some other display), the user would preferably move the laptop cursor in order to select (preferably by a "mouse click") the "sampled" peak or "median peak" response 310 as shown on the Response Graph 300 on FIG. 3. This activity is represented by the "User will Select Response Level with computer Mouse" block 470, and relatedly caused the APPLICATION to produce a "data point" (or "tick mark") 510 (associated with the response and the concentration level introduced) on the "Two-Point Calibration Graph" 500 shown in FIG. 5—and as represented by the "Plot Level Value on a Point Location Graph" block 480. Still continuing with the description, the user would them inject a known (preferably a high) concentration of the same stimulant (i.e., a "Standard Sample") into the inlet of the INSTRUMENT 220 (as represented by the "loop"485 and the "Inject" block 425). The TEST 400 would then be continued, as previously described, by repeating the steps between (and including) the "Collect Data" block 430 and "Plot Value on a Point Location Graph" block 480. After the TEST 400 repeats the above-described process for a second stimulant (i.e., after the second stimulant is run and a second "data point" 520 is generated), the TEST 400 preferably completes by: allowing the user to save portions of the data to a database and/or generate a report before stopping the Application 400, as represented by the User has Option to save Points to Database" block 490, the "User has Option to Run an Excel Based Report" block 492, and the "Stop Application" block 494. While using the Excel® application from the Microsoft Corporation may be preferable for at least generating reports, any other suitable application (and not only those applications limited to report generating) could be used as well.

Figure 5:
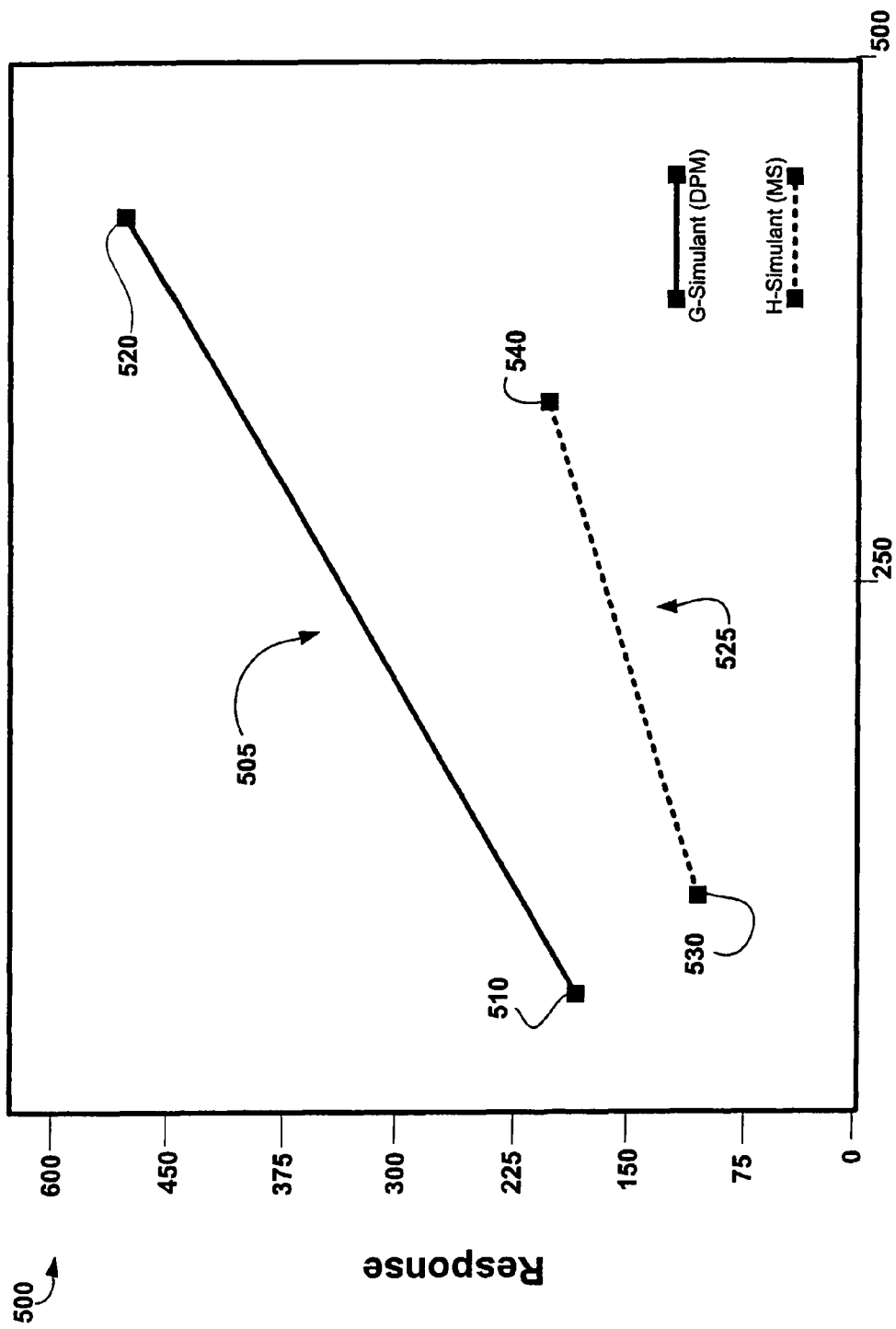
FIG. 5 is a graphical example of typical Two-Point Calibration Plots for a dual-cell detection instrument (as generated by the Process and System) according to a preferred embodiment of the present invention.

Referring now to FIG. 5, an example of a Two-Point Calibration Plot 500 associated with the response of each cell of a dual-cell detection Instrument 220 to the G-simulant (e.g., dipropylene glycol methyl ether (DPM")) and the H-simulant (e.g., methyl salicylate (MS)) (according to preferable use of the TEST 400 is shown). As shown, the G-simulant response is the upper Calibration Plot 505 having a low concentration "data point" 510 and a high concentration "data point" 520 while the H-simulant response is shown as the lower Calibration Plot 525 having a low concentration "data point" 530 and a high concentration "data point" 540. These Plots 505 and 525 can then be used for various diagnostic and/or testing purposes including, but not limited to, at least verifying the performance of the Instrument 220, which may be accomplished by comparing the above-described Calibration Plots 505 and 525 against known "calibration standard" plots (not shown), which may be stored on the laptop 205.

Figure 6:
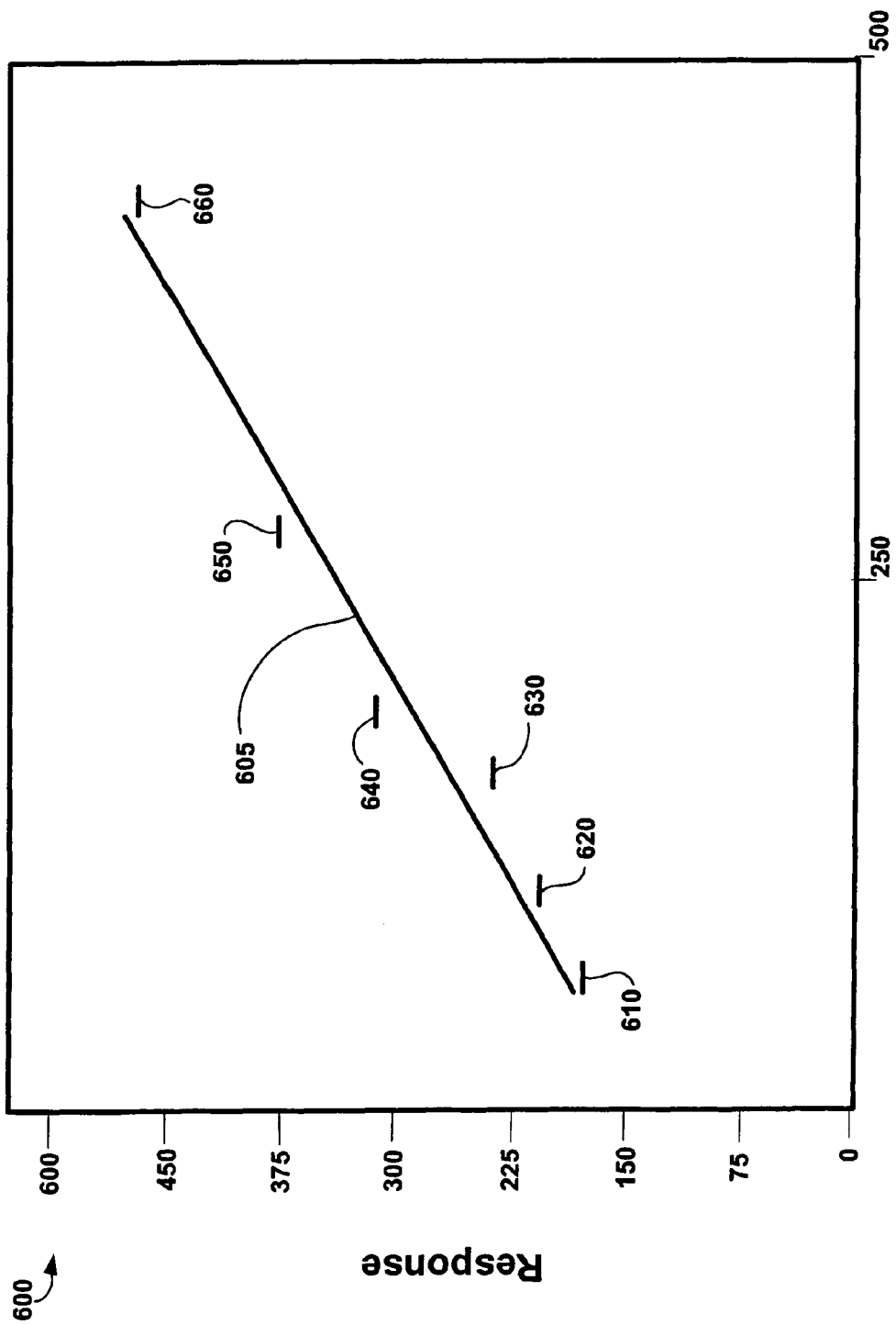
FIG. 6 is a graphical example of a Multiple Point Calibration Plot for a detection instrument (as generated by the Process and System) according to a preferred embodiment of the present invention.

Referring now to FIG. 6, another embodiment of a method that can be used to produce a Two-Point Calibration Plot 500 is shown. As shown, and as described below, only the steps used to make one of the above-described Calibration Plots is shown and described; however, it should be understood that these steps could be repeated (as described above) to produce multiple Calibration. Plots as well. As shown, multiple "data points" 610, 620, 630, 640, 650 and 660 are generated by injecting increasing concentrations of one stimulant into the Instrument Inlet 425, and by repeating TEST 400 steps 425, 430, 440, 450, 460, 470 and 485 for each different concentration being injected. After obtaining all of the "data points" desired, the user could run a statistical analysis routine to produce the Multiple Point Calibration Plot 605, which may be a best-fit plot based on regression analysis; however, any other suitable graph and/or plot generating application could be used as well.

In another embodiment of the System 200, the computing functions and/or the "Standard Sample" generating and introduction functions may be integrated into one self-contained unit, or either or both may be integrated within the Instrument Under Test 220 itself, which may allow for the full-automation of the testing, and may provide for the triggering of the tests and/or the transmission of the results to a remote site.

Finally, it will be apparent to those skilled in the art of vapor detection instruments or systems, related testing equipment, and/or other related fields, that many other modifications and/or substitutions can be made to the foregoing preferred embodiments without departing from the spirit and scope of the present invention. The preferred embodiments and the best mode of the present invention are described herein. However, it should be understood that the best mode for carrying out the invention herein described is by way of illustration and not by way of limitation. Therefore, it is intended that the scope of the present invention include all of the modifications that incorporate its principal design features, and that the scope and limitations of the present invention should be determined by the scope of the appended claims and their, equivalents.

What is claimed is:

1. A vapor detection instrument testing process, comprising the steps of:

connecting a computing system to a vapor detection instrument, wherein said computing system is loaded with testing software;

connecting a test substance generator for providing at least one test substance, to said vapor detection instrument;

starting said computing system and said vapor detection instrument;

verifying connections between said computing system and said vapor detection instrument;

starting said test substance generator;

injecting a known first concentration level of a first test substance into said vapor detection instrument;

operating said vapor detection instrument to perform a first analysis of said known first concentration level of said first test substance injected into said vapor detection instrument, and to generate a first response based on said first analysis;

operating said computing system to collect said first response into a first data stream of said computing system;

saving portions of said first computing system data stream in a computing system database;

generating portions of said first computing system data stream as a first response graph;

displaying said first response graph on a display of the computing system;

selecting, for said known first concentration level, a first peak level response point on said first response graph;

plotting and displaying said first peak level response point on a point location graph, wherein said point location graph is provided to a user by said display of the computing system;

injecting a known second concentration level of said first test substance into said vapor detection instrument, wherein said known second concentration level differs from said known first concentration level;

operating said vapor detection instrument to perform a second analysis of said known second concentration level of said first test substance injected into said vapor detection instrument and to generate a second response based on said second analysis;

operating said computing system to collect said second response from said vapor detection instrument and to convert said second response into a second computing system data stream;

saving portions of said second computing system datastream in a computing system database;

generating portions of said second computing system data stream as a second response graph;

displaying said second response graph on said computing system display;

selecting a second peak level response point on said second response graph;

plotting and displaying said second peak level response point on said point location graph, wherein said point location graph is provided to said user by said computing system display;

generating a first concentration level-second concentration level calibration graph, wherein said calibration graph is provided to said user by said computing system display; and, using said calibration graph to perform a performance check on said vapor detection instrument.

\* \* \* \* \*